United States Patent
Labyed

(10) Patent No.: US 11,678,862 B2
(45) Date of Patent: Jun. 20, 2023

(54) MUSCLE CONTRACTION STATE TRIGGERING OF QUANTITATIVE MEDICAL DIAGNOSTIC ULTRASOUND

(71) Applicant: Siemens Medical Solutions USA, Inc., Malvern, PA (US)

(72) Inventor: Yassin Labyed, Maple Valley, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 203 days.

(21) Appl. No.: 16/571,331

(22) Filed: Sep. 16, 2019

(65) Prior Publication Data
US 2021/0077067 A1   Mar. 18, 2021

(51) Int. Cl.
*A61B 8/00* (2006.01)
*A61B 8/14* (2006.01)
*A61B 8/08* (2006.01)

(52) U.S. Cl.
CPC .............. *A61B 8/145* (2013.01); *A61B 8/485* (2013.01); *A61B 8/5207* (2013.01); *A61B 8/5223* (2013.01); *A61B 8/543* (2013.01); *A61B 8/488* (2013.01); *A61B 8/5246* (2013.01)

(58) Field of Classification Search
CPC ....... A61B 8/145; A61B 8/485; A61B 8/5207; A61B 8/488; A61B 8/5246
See application file for complete search history.

(56) References Cited

U.S. PATENT DOCUMENTS

| | | | | |
|---|---|---|---|---|
| 5,097,836 A | * | 3/1992 | Yamada | A61B 8/08 600/443 |
| 5,846,200 A | * | 12/1998 | Schwartz | A61B 8/44 600/443 |
| 6,030,344 A | * | 2/2000 | Guracar | A61B 8/08 600/447 |
| 6,038,465 A | * | 3/2000 | Melton, Jr. | G01S 7/539 600/407 |
| 7,252,638 B2 | | 8/2007 | Kahn | |
| 9,168,021 B2 | | 10/2015 | Pernot | |
| 2001/0047130 A1 | * | 11/2001 | Walsh | A61B 5/055 600/407 |
| 2002/0151795 A1 | * | 10/2002 | Palti | A61B 8/06 600/454 |
| 2003/0158483 A1 | * | 8/2003 | Jackson | A61B 8/0883 600/449 |
| 2006/0247527 A1 | | 11/2006 | Maruyama | |

(Continued)

OTHER PUBLICATIONS

Tucker, "Anatomy, Blood Vessels, 2021" (Year: 2021).*

(Continued)

*Primary Examiner* — Katherine L Fernandez
*Assistant Examiner* — Brooke Lyn Klein

(57) ABSTRACT

For quantitative ultrasound imaging with a medical diagnostic ultrasound scanner, muscle tissue is scanned in order to determine the state of contraction. Once the desired state is identified, then QUS imaging is triggered to quantify or measure a tissue property while the muscle is in the desired state. The values of the tissue property at a known state of contraction may be more diagnostically useful or informative. Comparisons of the tissue property across time and/or location may more accurately reflect diagnostic information due to the triggering.

19 Claims, 1 Drawing Sheet

(56) References Cited

U.S. PATENT DOCUMENTS

| | | | |
|---|---|---|---|
| 2007/0078344 A1* | 4/2007 | Rafter | G01S 7/52041 |
| | | | 600/450 |
| 2008/0071174 A1* | 3/2008 | Waki | G16H 50/30 |
| | | | 600/442 |
| 2008/0139936 A1 | 6/2008 | Choi | |
| 2008/0249414 A1* | 10/2008 | Yang | A61B 8/0883 |
| | | | 600/445 |
| 2010/0240994 A1* | 9/2010 | Zheng | A61B 8/00 |
| | | | 600/440 |
| 2010/0312116 A1* | 12/2010 | Pernot | A61B 8/0883 |
| | | | 600/453 |
| 2011/0028838 A1* | 2/2011 | Pernot | A61B 5/015 |
| | | | 600/437 |
| 2011/0087118 A1* | 4/2011 | Patel | A61B 8/08 |
| | | | 600/509 |
| 2012/0116218 A1* | 5/2012 | Martin | A61B 8/463 |
| | | | 600/437 |
| 2012/0232387 A1* | 9/2012 | Miyachi | A61B 5/02007 |
| | | | 600/438 |
| 2013/0041477 A1* | 2/2013 | Sikdar | A61F 2/583 |
| | | | 623/57 |
| 2013/0085393 A1* | 4/2013 | Schauf | A61B 8/466 |
| | | | 600/447 |
| 2015/0099972 A1* | 4/2015 | Jacobson | G16H 50/30 |
| | | | 600/407 |
| 2015/0148674 A1* | 5/2015 | Park | A61B 8/463 |
| | | | 600/438 |
| 2015/0245820 A1* | 9/2015 | Tamada | A61B 8/0891 |
| | | | 600/449 |
| 2017/0181729 A1 | 6/2017 | Tanter | |
| 2019/0099162 A1* | 4/2019 | Keshet | G06T 7/0016 |
| 2020/0064469 A1* | 2/2020 | Trahey | G06N 7/01 |
| 2020/0085410 A1* | 3/2020 | Banjanin | A61B 5/0245 |
| 2021/0361262 A1* | 11/2021 | Xi | G01S 7/52022 |
| 2022/0192640 A1* | 6/2022 | Vignon | G01S 15/8993 |

OTHER PUBLICATIONS

Benjamin Wedro, Echocardiogram (Echocardiography) (Year: 2020).*
Brausch et al. "Classifying muscle states with ultrasonic single element transducer data using machine learning strategies", Sep. 3-6, 2019 (Year: 2019).*
Sikdar et al., "Quantification of Muscle Tissue Properties by Modeling the Statistics of Ultrasound Image Intensities using a Mixture of Gamma Distributions in Children With and Without Cerebral Palsy", Sep. 2018 (Year: 2018).*
Song, Pengfei, et al. "Quantitative assessment of left ventricular diastolic stiffness using cardiac shear wave elastography: a pilot study." Journal of Ultrasound in Medicine 35.7 (2016): 1419-1427.

* cited by examiner

MUSCLE CONTRACTION STATE TRIGGERING OF QUANTITATIVE MEDICAL DIAGNOSTIC ULTRASOUND

BACKGROUND

The present embodiments relate to medical diagnostic ultrasound. In particular, ultrasound is used to provide quantitative ultrasound (QUS) imaging. In QUS imaging, ultrasound information is further processed to quantify a biomarker or characteristic of the tissue being imaged. Rather than merely providing a B-mode image of the tissue, a characteristic of that tissue is imaged. For example, shear wave speed in the tissue is calculated using ultrasound imaging. Other examples include strain, attenuation, or backscatter measures.

QUS imaging enables assessment and comparison of tissue properties under varying conditions. One example includes shear wave speed or backscatter changes during cycles of muscle contraction and relaxation. Another example includes elasticity, fat fraction, shear wave viscosity, modulus, or backscatter coefficient measured for a muscle or between different tissues. For imaging the muscle, inconsistencies in quantification result from the measuring and/or comparing quantities from an unknown contraction state of the muscle.

SUMMARY

By way of introduction, the preferred embodiments described below include a method, system, computer readable medium, and instructions for quantitative ultrasound imaging with a medical diagnostic ultrasound scanner. Muscle tissue is scanned in order to determine the state of contraction. Once the desired state is identified, then QUS imaging is triggered to quantify or measure a tissue property while the muscle is in the desired state. The values of the tissue property at a known state of contraction may be more diagnostically useful or informative. Comparisons of the tissue property across time and/or location may more accurately reflect diagnostic information due to the triggering.

In a first aspect, a method is provided for quantitative ultrasound imaging with a medical diagnostic ultrasound scanner. The medical diagnostic ultrasound scanner scans muscle tissue of a patient with ultrasound. An image processor detects a contraction state of the muscle tissue with ultrasound data from the scanning. The image processor triggers the quantitative ultrasound imaging by the medical diagnostic ultrasound scanner. The quantitative ultrasound imaging is triggered in response to the detection of the contraction state. A quantitative ultrasound image from the triggered quantitative ultrasound imaging is displayed.

In a second aspect, a non-transitory computer readable storage medium has stored therein data representing instructions executable by a programmed processor for quantitative ultrasound imaging. The storage medium includes instructions for: triggering the quantitative ultrasound imaging in response to detection of a muscle contraction state; comparing a first quantity from the triggered quantitative ultrasound imaging to a second quantity; and generating an image showing the comparison.

In a third aspect, a system is provided for triggering quantitative ultrasound imaging. A transmit beamformer is configured to transmit ultrasound in a patient. A receive beamformer is configured to output samples from echoes of the ultrasound. An image processor is configured to determine a state of a muscle from the output samples or data from detection of the output samples of first scanning by the transmit and receive beamformers, configured to cause the transmit and receive beamformers to perform second scanning based on the state of the muscle, the second scanning for the quantitative ultrasound imaging, and configured to determine a value for a tissue property from the quantitative ultrasound imaging. A display is configured to display the value of the tissue property.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A muscle contraction state is automatically detected and triggers shear wave and/or backscatter acquisitions. The detection of contraction state is based on: radio frequency (RF) and/or image analysis to estimate tissue motion, deformation, or strain (speckle tracking, normalized cross correlation, etc. . . . ) A trained artificial intelligence algorithm (machine-learned model) may detect the contraction state from RF, image, and/or video (e.g., sequence) data. The triggered QUS uses specialized (e.g., fixed) sequences triggered based on the detected muscle contraction state. An analysis tool provides measurement information of shear wave and/or backscatter-based tissue properties during a known muscle contraction or loading cycle.

Figure 1:
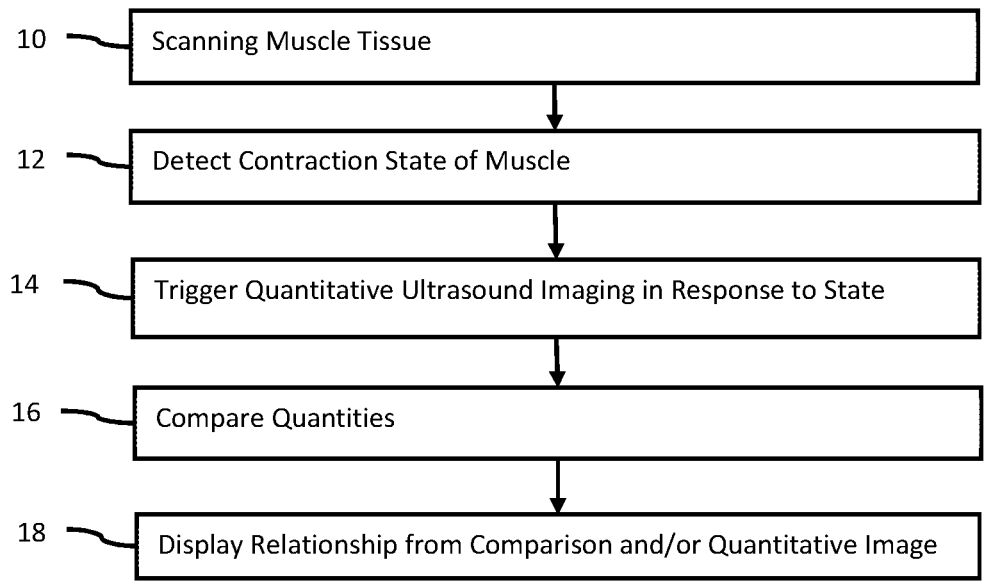
FIG. 1 is a flow chart of one embodiment of a method for quantitative ultrasound imaging with a medical diagnostic ultrasound scanner.

FIG. 1 shows one embodiment of a flow chart diagram of a method for QUS imaging with a medical diagnostic ultrasound scanner. The muscle contraction state is automatically detected. Shear wave, backscatter, and/or other QUS acquisitions are triggered based on detection of a given contraction state.

Figure 2:
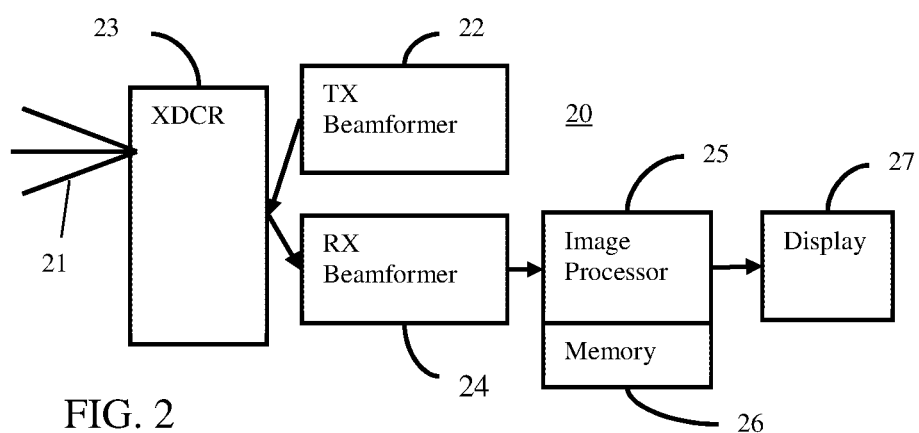
FIG. 2 is a block diagram of one embodiment of a system for triggered quantitative ultrasound imaging.

The method is performed by the ultrasound imaging system 20 of FIG. 2, the image processor 25, or a different system and/or processor. For example, the ultrasound imaging system 20 scans, detects, triggers itself to perform QUS, compares quantities, and displays the relationship from the comparison.

The acts of FIG. 1 are performed in the order shown (top to bottom) or a different order. For example, a QUS image may be displayed in act 18 prior to comparison of quantities of act 16.

Additional, different, or fewer acts than shown in FIG. 1 may be used. For example, act 16 is not performed. As another example, acts for scanning and generating B-mode or other ultrasound images for identifying a region of interest may be added.

In act 10, the medical diagnostic ultrasound scanner scans muscle tissue of a patient. A transducer is positioned relative to the patient. The ultrasound scanner scans a planar area or volume region of the patient including muscle tissue. For example, the transducer is positioned by an arm or leg. The user activates scanning. Acoustic energy is transmitted into the patient, and acoustic echoes are received. The echoes are beamformed to sample the scan region.

Any type of scanning may be used. For example, B-mode scanning is used. B-mode images are generated to view the interior of the patient, allowing the user to indicate a region of muscle tissue as a region of interest. Alternatively, an image processor detects the region of muscle tissue from beamformed samples, detected data, and/or image data.

The scanning occurs once, or a sequence of scans is performed. For example, the scanning is repeated in an ongoing or interleaved manner. Any frame rate may be used, such as 20 Hz or more.

In act 12, an image processor detects a contraction state of the muscle tissue with ultrasound data from the scanning. The ultrasound data used for detection is from the scanning. Beamformed data prior to detection (e.g., prior to B-mode or intensity detection) may be used. For example, radio frequency or in-phase and quadrature data for beamformed samples are used. Detected or image data, such as B-mode data, may be used. The image data may be after detection (e.g., B-mode or intensity detection) and from before scan conversion and/or display mapping. Image data after scan conversion and/or display mapping may be used.

The detection is from a frame of data, such as representing the patient at a particular time or period. In other embodiments, a sequence of frames (e.g., video data or frames of ultrasound data over time) is used. Change over time or between frames of ultrasound data is used to detect the contraction state.

In one embodiment, the detection of the contraction state is based on tissue motion. The patient is asked to move. The scanning of the muscle occurs during the movement. The motion of the tissue during the movement is detected to determine the contraction state. For example, speckle tracking, normalized cross-correlation, correlation, or other similarity measure are used to determine a change in position, strain, expansion, or reduction in the muscle tissue over time. The similarities for one or more localized regions over time are determined.

One, two, or three-dimensional tissue motion tracking may be used. For example, the tissue motion is tracked with correlation along scan lines for one-dimensional detection.

The variance over time indicates the muscle contraction state. For example, maximum expansion corresponds to a loaded or contracted state while the minimum expansion corresponds to an unloaded or relaxed state.

In other embodiments, image processing is used. For example, the muscle is segmented. The change in shape or the shape of the muscle may be used to determine the contraction state, such as by template matching.

In another embodiment, a sequence of frames of ultrasound data from repetitive performance of scanning is used to detect the contraction state. The sequence is input to a machine-learned model. The machine-learned model is trained from training data to detect the contraction state and/or to identify when in the sequence the contraction state has a given value, such as relaxed or loaded. The machine-learned model is a neural network, support vector machine, or other machine learning model. Training data of many samples of sequences with ground truth contraction states for each frame of the sequence is used to machine train the model. Once trained, the machine-learned model indicates or detects the contraction state based on input of ultrasound data of a sequence for a patient. In alternative embodiments, the machine-learned model is trained to output the contraction state given input of one frame of ultrasound data.

The contraction state is detected as contracted or loaded, relaxed, or an in-between state. The level or amount of contraction, such as between a range from relaxed to fully loaded may be determined as the contraction state. In one embodiment, a binary determination is made between contracted and relaxed. The contraction state over time may be determined.

In act 14, the image processor triggers the QUS imaging in response to detection of a muscle contraction state. The QUS is to be performed at a particular contraction state, such as quantifying a tissue property while the muscle is in the loaded and/or relaxed state. Alternatively, the QUS is to be performed over time to measure values of the tissue property where the values are related to various contraction states over that time.

The medical diagnostic ultrasound scanner is triggered to perform the QUS. In response to detection of the contraction state from correlation or speckle tracking of radio frequency ultrasound data or image ultrasound data, in response to detection by the machine-learned model, or other detection of the contraction state, the scanner is triggered to perform QUS.

The triggering is immediate or within a short time period (e.g., 0.5 seconds). Before the muscle contraction state changes or changes much, the QUS is performed. Alternatively, the triggering is delayed, such as using previous cycles of contraction state variation to predict when the muscle will be in a desired contraction state. In another embodiment, the triggering confirms contraction change so that continued QUS is triggered (i.e., not stopped).

Once triggered, the ultrasound scanner transmits and receives acoustic energy and calculates a value or values of one or more tissue properties. The tissue properties are measured for a location, along a line, over an area, or throughout a volume. The QUS is performed for any region of interest, such as a region of interest for the muscle.

Any type of QUS may be performed. For example, shear wave imaging is performed. An acoustic radiation force impulse is transmitted. In response, a shear wave is created in the tissue. The shear wave propagates from an origin. Ultrasound scanning is used to track tissue displacements from the shear wave. The shear wave velocity in the tissue is determined based on the displacements. Other tissue properties may be determined from the shear wave and/or shear wave velocity, such as Young's modulus, viscoelastic property, and/or attenuation. As another example, elasticity, attenuation, or strain imaging is performed.

In one embodiment, backscatter imaging is performed as the triggered QUS. For backscatter coefficient or attenuation quantification, a B-mode scan is performed. Rather than performing B-mode detection (e.g., detecting the power or intensity of the return signal), the beamformed samples prior to detection are processed. A power spectrum of the return signal as a function of time is created with a fast Fourier transform. The change by depth gives attenuation, such as based on an exponential fit. Attenuation compensation is then applied to determine the power of the signal at the target as the backscatter coefficient. The backscatter coefficient as a function of frequency may be used to determine scatter.

The QUS imaging may rely on calibration or information specific to settings used in QUS imaging. For example, a given intensity of ARFI or a calibration from phantom imaging is used. To avoid errors due to changes, the scan sequence and/or imaging processing for QUS may be set.

The triggered sequence for scanning is based on the muscle contraction state. The sequence is specific to the state. Rather than allowing user change, the triggered scanning is set or fixed. In alternative embodiments, the user may set one or more scanning or image processing settings.

In act 16, the image processor compares a quantity from the triggered QUS to another quantity. A relationship between quantities is determined. The relationship may be a difference, a ratio, or other function. The relationship is calculated.

The relationship is an analysis tool that provides measurement information for tissue properties during muscle contraction or loading cycle or at another muscle state. Online or offline analysis of the QUS measurements (e.g., QUS images or values) is provided.

The comparison is performed for quantities at different locations, times, and/or under different conditions. Where there are two regions, the relationship compares the quantity for one region to the quantity for the other region, such as different parts of the muscle, different muscles, muscles in different contraction states, or muscle verses other type of tissue. Relationships between three or more regions may be determined as different sets of relationships or a single relationship between the three or more regions. The relationship between the quantities at different frequencies may be determined. The relationship between the quantities at different times may be determined. For example, the relationship between backscatter coefficient for the same muscle tissue during contraction and as relaxed is determined. For backscatter, the relationship may be between spectra.

In act 18, the image processor generates an image. The image is a QUS image, such as a shear wave velocity or a backscatter coefficient image. The QUS image includes the values of the quantitative parameter or parameters. For example, the shear wave velocity as a function of location in one, two, or three dimensions is included in the QUS image. Image is used to reflect ultrasound data that may be used to form a display image or ultrasound data formatted to be or that has been displayed. The shear wave, backscatter, or other QUS imaging may determine values for tissue properties for a location or a plurality of locations in one, two, or three dimensions. In another example, the QUS image includes one quantitative value for an entire ROI or a location (e.g., point).

The QUS image may include other information. For example, QUS values are used for a region of interest, and locations in the field of view outside the region of interest are formed from the B-mode image.

The QUS image may show results of the comparison. For example, the value of the ratio or difference with or without also showing the two quantities is displayed as part of the image. The results may be an annotation, graph, highlighting, or mapping. For example, muscle tissue with the quantity and/or comparison result above or below a threshold is highlighted or distinguished from other tissue to indicate the quantity or comparison result being above or below the threshold.

The comparison results, quantity, quantities, and/or information derived therefrom may be displayed as annotation (e.g., alphanumeric text), graphs, and/or mapping of color to pixels. The image may also show the contraction state detected for the muscle. For example, an annotation is provided as a label indicating the contraction state and the quantity from the QUS measurement.

The image is on a display, such as a display of the ultrasound scanner. The image may be transferred over a computer network and/or stored in a memory, such as a patient electronic health record or a picture archiving and communication system database.

FIG. 2 shows one embodiment of a medical system 20 for triggering QUS imaging. The medical system 20 is an ultrasound scanner for detecting a contraction state of muscle and responding with QUS imaging or measurement based on (triggered and/or labeled) the contraction state. The medical system 20 implements the method of FIG. 1 or another method.

The medical system 20 includes a transmit beamformer 22, a transducer 23, a receive beamformer 24, a image processor 25, a memory 26, and a display 27. Additional, different or fewer components may be provided. For example, the medical system 20 includes a B-mode or other detector separate from the image processor 25. As another example, the image processor 25, memory 26, and/or display 27 are provided without the front-end components, such as the transmit and receive beamformers 12, 16. In yet another example, a user interface including a user input (e.g., mouse, trackball, keyboard, buttons, knobs, sliders, and/or touch pad) is provided for user indication of a region of interest or other input.

In one embodiment, the medical system 20 is a medical diagnostic ultrasound system. In an alternative embodiment, the system 20 is a computer or workstation.

The transducer 23 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 23 connects with the transmit beamformer 22 and the receive beamformer 24 through a transmit/receive switch, but separate connections may be used in other embodiments.

The transmit and receive beamformers 22, 24 are a beamformer for scanning with the transducer 23. The transmit beamformer 22, using the transducer 23, transmits one or more beams to scan a region. Vector®, sector, linear or other scan formats may be used. The receive lines and/or transmit beams are distributed in the scan region. The receive beamformer 24 samples the receive beams at different depths.

The transmit beamformer 22 is a processor, delay, filter, waveform generator, memory, phase rotator, digital-to-analog converter, amplifier, combinations thereof or any other now known or later developed transmit beamformer components. In one embodiment, the transmit beamformer 22 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 22 is configured as a plurality of channels for generating electrical signals of a transmit waveform for each element of a transmit aperture on the transducer 23. The waveforms are unipolar, bipolar, stepped, sinusoidal, or other waveforms of a desired center frequency or frequency band with one, multiple or fractional number of cycles. The waveforms have relative delay and/or phasing and amplitude for focusing the acoustic energy. The transmit beamformer 22 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, and/or combinations thereof. An amplitude may be altered or set. A transmit beam origin, orientation, and focus are generated based on these beamforming parameters.

The receive beamformer 24 is a preamplifier, filter, phase rotator, delay, summer, base band filter, processor, buffers, memory, combinations thereof or other now known or later developed receive beamformer components. The receive beamformer 24 is configured into a plurality of channels for receiving electrical signals representing echoes or acoustic energy impinging on the transducer 23. A channel from each of the elements of the receive aperture within the transducer 23 connects to an amplifier and/or delay. An analog-to-digital converter digitizes the amplified echo signal. The digital radio frequency received data is demodulated to a base band frequency. Any receive delays, such as dynamic receive delays and/or phase rotations, are then applied by the amplifier and/or delay. A digital or analog summer combines data from different channels of the receive aperture to form one or a plurality of receive beams. The summer is a single summer or cascaded summer. In one embodiment, the beamform summer is configured to sum in-phase and quadrature channel data in a complex manner such that phase information is maintained for the formed beam. In alternative embodiments, the receive beamformer sums radio frequency data. Other receive beamformers may be used.

The receive beamformer 24 is configured to form receive beams in response to the transmit beams. For example, the receive beamformer 24 receives one, two, or more receive beams in response to each transmit beam. The phase rotators, delays, and/or summers may be repeated for parallel receive beamformation. One or more of the parallel receive beamformers may share parts of channels, such as sharing initial amplification. The receive beams are collinear, parallel and offset or nonparallel with the corresponding transmit beams.

The receive beamformer 24 is configured to output samples for a location or different locations in a patient. The receive beamformer 24 outputs spatial samples representing different spatial locations of a scanned region or samples representing one location. Once the channel data is beamformed or otherwise combined to represent spatial locations along the scan lines 21, the data is converted from the channel domain to the image data domain. By scanning with transmit and receive beamformation in any pattern (e.g., sector, Vector, or linear), a field of view is scanned.

The transmit and receive beamformers 22, 24 are configured to scan in various modes. For example, B-mode scanning is performed for detecting contraction state. As another example, transmit and receive sequences are performed for QUS. A beamformer controller configures the beamformers 22, 24 to scan in a given mode, such as repetitive B-mode scanning until detection of muscle contraction in a given state, and then QUS scanning alone or interleaved with B-mode scanning is performed while the muscle is in the desired state or states.

The image processor 25 is a digital signal processor, a general processor, an application specific integrated circuit (ASIC), field programmable gate array (FPGA), artificial intelligence processor, control processor, digital circuitry, analog circuitry, graphics processing unit, combinations thereof, or other now known or later developed device for calculating quantities in QUS and determining relationships between quantities. The image processor 25 is configured by hardware, firmware, and/or software, such as operating pursuant to instruction provided in the memory 26 or a different memory. In one embodiment, the image processor 25 is a digital signal processor, ASIC, or FPGA specifically for applying a Fourier transform, and another device (e.g., calculator or processor) calculates a backscatter coefficient from an output of the transform device. In other embodiments, the image processor 25 is a programmable device that performs image processing for shear wave, strain, elasticity, and/or other QUS imaging.

The image processor 25 is configured to determine a state of a muscle from (1) the output samples or (2) data from detection of the output samples. The image processor 25 determines the state from beamformed samples (e.g., radio frequency or in-phase and quadrature information) or from image data after detection (e.g., after B-mode detection). The state is determined by speckle tracking, correlation, or other similarity measure along one, two, or three dimensions. Other detection may be used. A shape (e.g., segmentation) may be identified, and the contraction state detected based on the shape. In one embodiment, a machine-learned detector determines the contraction state and/or identifies one or more times or frames of data in a sequence representing the muscle in a given contraction state in response to input of a frame of ultrasound data (e.g., image frame) or a sequence of such frames.

The image processor 25 is configured to cause the transmit and receive beamformers 22, 24 to perform scanning based on the state of the muscle. The image processor 25 controls the scanning to provide QUS for the muscle when in a desired state. The QUS scanning is triggered based on the detection.

The image processor 25 is configured to determine a value for a tissue property from the QUS imaging. Beamformed samples for one or more locations are acquired. Before detection, the samples are used to calculate a quantity. In alternative embodiments, the quantity is calculated from image data after detection.

A value or values for any tissue property are quantified. For example, strain, elasticity, backscatter coefficient, scatter, attenuation, viscoelasticity, Young's modulus, shear wave velocity, or another type of tissue property is calculated. A value is determined for one location or representative of a group of locations. Values may be calculated for different times and/or locations.

In one embodiment, the image processor 25 is configured to determine a relationship between the value for the tissue property and another value for the tissue property from a different time or location. A ratio, difference, or other relationship between quantities over time and/or location is found. For spectral information, a ratio of spectra may be determined. A frequency-dependent relationship may be determined.

The ultrasound data and/or quantities may be used to generate an image. A B-mode detector, flow estimator (e.g., Doppler processor), or other detector may be provided for detecting characteristics from the receive beamformed samples. A B-mode detector detects the intensity or power of the acoustic backscatter. A flow estimator detects the velocity, energy, or variance of moving objects (e.g., tissue or fluid). The detection may be used to generate an image from which regions of interest are selected. QUS provides a value or values for a region of interest. The value or values may be displayed separately from other modalities of imaging or may be overlaid, such as a color overlay or annotation on a B-mode image.

The image processor 25 is configured to generate an image. The image includes a value of a quantity of the tissue property, a multiple of such values from different locations or time, and/or a relationship between values (e.g., ratio). For example, a graph of the backscatter coefficient as a function of time is generated as an image. As another example, alphanumeric text is generated as an image, such as an alphanumeric text providing the value of the tissue property from QUS for muscle. A table may be generated. In another embodiment, the tissue property as a function of location within one or more regions of interest are mapped to colors or grayscale, which mapped values are used to generate a one, two, or three-dimensional distribution of the values in the muscle tissue.

The memory 26 is video random-access memory, random access memory, removable media (e.g. diskette or compact disc), hard drive, database, or other memory device for storing samples, spectra, values of quantities representing tissue properties, relationships between quantities, and/or images. The memory 26 is used by the image processor 25 for muscle contraction state triggered QUS or other acts described for FIG. 1.

The instructions for implementing the processes, methods and/or techniques discussed above (e.g., QUS imaging triggered based on contraction state of muscle) are provided on computer-readable storage media or memories, such as a cache, buffer, RAM, removable media, hard drive or other computer readable storage media, such as represented by the memory 26. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 27 is a CRT, LCD, plasma, projector, monitor, printer, touch screen, or other now known or later developed display device. The display 27 receives RGB, other color values, or other values and outputs an image. The image may be a gray scale or color image. The image displays information that is a function of the QUS, such as displaying one or more values of tissue property of muscle in a given state. A value or values for a relationship of the values from different times and/or locations may be displayed. Alphanumeric, graphical, annotation, or other representation of the value or values are displayed in an image on the display 27. The image may or may not additionally represent the region of the patient scanned by the beamformer 22, 16 and transducer 23.

In one embodiment, an image representing at least one of the regions of interest is annotated or color coded to indicate a level of the of the value to a reference. For example, different ranges of the tissue property represent different stages of a disease of the muscle. The image of or region of interest is color coded with a colors, shade, or brightness representing a given stage. Different colors, shades, and/or brightnesses represent different disease stages. The stage for that patient is indicated by color or other modulation of the region pixels. Textual indication may be used.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for Quantitative Ultrasound (QUS) imaging with a medical diagnostic ultrasound scanner, the method comprising:
   scanning, by the medical diagnostic ultrasound scanner, muscle tissue of a leg or arm of a patient with ultrasound;
   detecting, by an image processor, a contraction state of the scanned muscle tissue with ultrasound data from the scanning, the detecting being by change in the scanned muscle tissue;
   triggering, by the image processor, the QUS imaging by the medical diagnostic ultrasound scanner, the QUS imaging triggered in response to the detection of the contraction state of the scanned muscle tissue, the contraction state causing the triggering, the QUS imaging including an acoustic radiation force pulse; and
   displaying a QUS image from the triggered QUS imaging, the QUS image representing a tissue property of the muscle tissue of the arm or leg.

2. The method of claim 1 wherein the detecting comprises detecting the contraction state based on tissue motion.

3. The method of claim 1 wherein the detecting comprises detecting the contraction state from the ultrasound data, the ultrasound data is beamformed data as output by a beamformer.

4. The method of claim 1 wherein the detecting comprises detecting with the ultrasound data comprising image data.

5. The method of claim 1 wherein the detecting comprises detecting the contraction state based on tissue motion determined with speckle tracking or correlation, the tissue motion being of the arm or leg and in response to a request of movement of the arm or leg.

6. The method of claim 1 wherein the detecting comprises detecting with input of a sequence from repetitive performance of the scanning as the ultrasound data to a machine-learned model, the machine-learned model having been trained to detect the contraction state based on the input of the ultrasound data.

7. The method of claim 1 wherein the detecting comprises detecting the contraction state as a contracted state, and wherein the triggering comprises triggering the QUS imaging of the muscle in the contracted state.

8. The method of claim 1 wherein the detecting comprise detecting the contraction state as a relaxed state, and wherein the triggering comprises triggering the QUS imaging of the muscle in the relaxed state.

9. The method of claim 1 wherein the triggering comprises triggering shear wave imaging as the QUS imaging, and wherein the displaying comprises displaying a shear wave image as the QUS image.

10. The method of claim 1 further comprising calculating a relationship of a first quantity from the triggered QUS imaging to a second quantity, and wherein the displaying the QUS image comprises displaying the relationship.

11. A non-transitory computer readable storage medium having stored therein data representing instructions executable by a programmed processor for Quantitative Ultrasound (QUS) imaging, the storage medium comprising instructions for:

triggering the QUS imaging in response to detection of a muscle contraction state of muscle tissue of a leg or arm of a patient from ultrasound data, the muscle contraction state as contracted causing the triggering, the QUS imaging including an acoustic radiation force pulse and providing values of tissue property at different locations representing a spatial distribution of the tissue property;

comparing a first quantity from the triggered QUS imaging to a second quantity; and generating an image showing the comparison.

12. The non-transitory computer readable storage medium of claim 11, wherein the triggering comprises triggering upon the detection of the muscle contraction state from correlation or speckle tracking of radio frequency ultrasound data or image ultrasound data as the ultrasound data from ultrasound scanning prior to the triggering, the contraction state caused by requested patient movement of an arm or leg.

13. The non-transitory computer readable storage medium of claim 11, wherein the detection is performed by a machine-learned model.

14. The non-transitory computer readable storage medium of claim 11, wherein the triggering comprises triggering shear wave as the QUS imaging, and wherein the generating the image comprises generating the image as an image of the tissue property from the shear wave.

15. The non-transitory computer readable storage medium of claim 11, wherein the comparing comprises determining a ratio.

16. The non-transitory computer readable storage medium of claim 11, wherein the comparing comprises comparing the first quantity for a first location and the second quantity in a second location and/or comparing the first quantity for a first time and the second quantity for a second time.

17. A system for triggering Quantitative Ultrasound (QUS) imaging, the system comprising:

a transmit beamformer configured to transmit ultrasound in a patient;

a receive beamformer configured to output samples from echoes of the ultrasound;

an image processor configured to determine a state of a muscle of a leg or arm from the output samples or data from detection of the output samples of first scanning by the transmit and receive beamformers, configured to cause the transmit and receive beamformers to then perform second scanning including transmission of acoustic radiation force, the second scanning performed based on the determined state of the muscle, when the state of the muscle is at a value causing the second scanning, the second scanning for the QUS imaging representing a tissue property, and configured to determine a value for the tissue property from the QUS imaging; and a display configured to display the value of the tissue property.

18. The system of claim 17 wherein the image processor is configured to determine a relationship between the value for the tissue property, the tissue property being of the leg or arm muscle, and another value for the tissue property from a different time or location, and wherein the display is configured to display the relationship.

19. The system of claim 17 wherein the image processor is configured to determine the state from speckle tracking, correlation, or a machine-learned detector.

* * * * *